United States Patent
Furey (10) Patent No.: US 9,649,187 B2
(45) Date of Patent: May 16, 2017

(54) IMPLANTABLE FLOW DIVERTER

(71) Applicant: COOK MEDICAL TECHNOLOGIES LLC, Bloomington, IN (US)

(72) Inventor: Aidan Furey, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/276,448

(22) Filed: May 13, 2014

(65) Prior Publication Data

US 2014/0343664 A1   Nov. 20, 2014

(30) Foreign Application Priority Data

May 14, 2013  (GB) .................................. 1308652.5

(51) Int. Cl.
  *A61F 2/06*  (2013.01)
  *A61F 2/91*  (2013.01)
  *A61B 17/12*  (2006.01)
(52) U.S. Cl.
  CPC .......... *A61F 2/06* (2013.01); *A61B 17/12113* (2013.01); *A61B 17/12145* (2013.01); *A61F 2/91* (2013.01); *A61F 2002/068* (2013.01)
(58) Field of Classification Search
  CPC ................................ A61F 2/24; A61F 2/2475
  USPC ....................... 623/1.24, 2.1–2.19
  See application file for complete search history.

(56) References Cited

U.S. PATENT DOCUMENTS

| 7,815,673 B2* | 10/2010 | Bloom ................. A61F 2/2418 623/1.15 |
| 7,967,853 B2* | 6/2011 | Eidenschink ......... A61F 2/2418 623/1.24 |
| 2002/0179166 A1 | 12/2002 | Houston et al. |
| 2002/0198591 A1 | 12/2002 | Stergiopulos |
| 2003/0100945 A1 | 5/2003 | Yodfat et al. |
| 2003/0204243 A1* | 10/2003 | Shiu .......................... A61F 2/07 623/1.16 |
| 2003/0209835 A1* | 11/2003 | Chun .................... A61F 2/2412 264/339 |
| 2006/0259134 A1* | 11/2006 | Schwammenthal ...... A61F 2/24 623/2.11 |

(Continued)

FOREIGN PATENT DOCUMENTS

| DE | 597 472 | 2/1936 |
| EP | 1139917 A2 | 10/2001 |

(Continued)

*Primary Examiner* — Suzette J Gherbi
(74) *Attorney, Agent, or Firm* — Brinks Gilson & Lione (57) ABSTRACT

A flow diverter for implantation into a patient's vessel includes a distal annular support element and a proximal annular support element, the proximal and distal support elements supporting a longitudinally twisted diverter element. The flow diverter is designed to be disposed within a vessel and to impart a rotational or twisting motion to the flow of blood passing therethrough, thereby to reduce the pressure of blood at the center of the vessel. Such flow diversion can reduce the pressure of blood impinging upon an aneurysm at a bifurcation downstream of the vessel. The device can be particularly useful for the treatment of aneurysms occurring at the bifurcation between the basilar artery and the posterior cerebral arteries.

20 Claims, 7 Drawing Sheets

(56) References Cited

U.S. PATENT DOCUMENTS

| | | | | |
|---|---|---|---|---|
| 2007/0288086 A1* | 12/2007 | Kalmann | ............. | A61F 2/2418 623/1.24 |
| 2010/0106180 A1 | 4/2010 | Strother et al. | | |
| 2011/0066224 A1* | 3/2011 | White | ............. | A61F 2/2412 623/1.15 |
| 2013/0123908 A1* | 5/2013 | Hinchliffe | ............. | A61F 2/2475 623/1.24 |
| 2014/0296965 A1* | 10/2014 | Poor | ............. | A61F 2/915 623/1.15 |
| 2015/0032200 A1* | 1/2015 | Cottone | ............. | A61F 2/91 623/1.16 |

FOREIGN PATENT DOCUMENTS

| | | |
|---|---|---|
| GB | 2 382 776 A | 6/2003 |
| WO | WO 2012/102919 | 8/2012 |

\* cited by examiner

IMPLANTABLE FLOW DIVERTER

CROSS-REFERENCE TO RELATED APPLICATIONS

This application claims the benefit of priority under 35 U.S.C. §119(a) to Great Britain Patent Application No. 1308652.5, filed May 14, 2013, which is incorporated by reference here in its entirety.

TECHNICAL FIELD

The present disclosure relates to an implantable medical device, in particular for diverting flow within the vessel of a patient.

BACKGROUND ART

Many factors contribute to the formation of saccular aneurysms, particularly neural aneurysms. One of the major contributors is wall shear stress (WSS), which in addition to hypertension leads to a reduction in the elastic tissue of the tunica media, thereby contributing to the formation of the aneurysm. The effect of wall shear stress is heightened at certain anatomical geometries such as bifurcations, and for instance at the point where the basilar artery (BA) divides into the posterior cerebral arteries (PCA).

It is known to try to treat aneurysms by filling the aneurysmal sac with a filler such as a prosthetic coil. The methodology behind the use of prosthetic coils is to establish a hard thrombus formation within the sac of the aneurysm as a means of isolating the aneurysm wall from the flow of blood. While this can be effective in the treatment of many types of aneurysm, it is less effective when the aneurysm occurs at a bifurcation or trifurcation, such as at the base of the basilar artery.

It is also known to close off the entrance to the aneurysmal sac or to divert the flow of fluid therefrom, but known devices are not general suitable for treatment of aneurysms at the base of the basilar artery.

Examples of devices for treating aneurysms can be found in US-2002/0179166, US-2002/0198591, US-2003/0100945, US-2010/0106180 and WO-2012/102919.

SUMMARY OF THE INVENTION

The present disclosure seeks to provide improved treatment of aneurysms, in particular an implantable flow diverter and method of diverting flow from an aneurysm.

According to an aspect of the present invention, there is provided an endoluminal flow diverter that comprises a central axis, a pair of supports, and a diverter element. The central axis runs through a diameter of the device and along a longitudinal direction. The device further comprises a pair of supports being a proximal and distal support spaced in the longitudinal direction along a length of the device. The device further comprises a diverter element being disposed between and supported by the proximal and distal supports.

The diverter element comprises a panel being twisted in the longitudinal direction and extending across the diameter, wherein the panel twists by an angle of about 90 degrees between the proximal and distal supports.

The flow diverter has a structure which enables it to divert the flow of blood within a vessel, in particular to reduce the flow at the central portion of the vessel by causing the pressure of blood to even out across substantially the entire width of the vessel. When disposed, for example, at the base of the basilar artery, that is by the posterior cerebral arteries, this has the effect of reducing the pressure of blood flow to the vessel wall at the bifurcation and opposite the basilar artery. This can reduce the pressure of blood into an aneurysmal sac and therefore assist in the treatment of such an aneurysm.

Advantageously, the panel is formed of a sheet of material. The panel is preferably substantially impermeable, that it has a structure which acts as a barrier to blood therethrough such that all or substantially all of any blood impinging on the panel is diverted by the panel. In some embodiments the panel may include perforations or slots therein. The slots or perforations can increase the ability of the panel to twist, or over twist, so as to compress the device radially for deployment purposes. The slots or perforations are, though, preferably small enough to retain the barrier effect of the panel, that is to prevent or substantially flow of fluid through the panel. The, panel provides a surface within which the perforations or slots are disposed, the surface providing a barrier to blood therethrough.

Preferably, the panel extends substantially across the diameter of the device. It may extend across the entirety of the diameter of the device or almost across its entirety, any shortfall being taken up in practice by the conformability of the vessel wall.

Preferably, the panel is of substantially uniform thickness. In practice, it is preferred that the panel is of thin construction, which will have little or no effect on the overall blood pressure, that it will not cause an increase in blood pressure as a result of vessel constriction, which is a characteristic of some implantable medical devices. In the preferred embodiment, the panel extends across the central axis of the device.

Advantageously, the panel twists uniformly in helical manner in the longitudinal direction of the device. Preferably, the panel twists in the longitudinal direction of the device by an angle of around 90 degrees between the proximal and distal supports. It has been found that this feature provides optimal flow diversion. In an embodiment, the panel is substantially rectangular.

Preferably, the proximal and distal supports are ring-shaped. They may be separate from one another, although in other embodiments they may be connected to one another.

Also described is a method of diverting fluid flow in a vessel including the following steps. A user deploys in a vessel an endoluminal flow diverter as described above. Deployment of the flow diverter causes blood flow in the vessel to be diverted by twisting the flow in the vessel.

Advantageously the panel extends across the central axis of the device, the method providing for flow in the center of the vessel to be diverted. In the preferred embodiment, the method reduces the flow of fluid in the center of the vessel and most preferably evens the flow of fluid across the width of the vessel.

Other features are disclosed in the description of the preferred embodiments of the invention which follows. It is to be understood that all such features are applicable to all embodiments disclosed herein.

DESCRIPTION OF THE PREFERRED EMBODIMENTS

Described below are various embodiments of flow diverter for diverting flow within a patient's vessel. The term flow diverter as used herein encompasses the guiding of the flow of blood within a vessel, in particular to alter the pressure profile across the diameter of the vessel and in the preferred embodiments to reduce the pressure flow at the center of the vessel and preferably so as to even out the flow pressure across the diameter of the vessel.

As will be appreciated from the disclosure of the preferred embodiments set out below and in the accompanying drawings, these provide a flow diverter which has the same or substantially the same cross-sectional area at the proximal and distal ends of the device, that is at the inlet and outlet of the device. As a result of this, there is no change in the overall volume of fluid passing through the flow diverter and no overall change in pressure of fluid passing through the diverter. Experimental data has shown that the preferred embodiments of flow diverter disclosed herein are able to effect a tenfold decrease in pressure within an aneurysm. As a result, there is no flow or virtually no flow of fluid within the aneurysm.

The preferred embodiments are described in connection with a flow diverter intended for implantation in the basilar artery and in particular adjacent to the bifurcation with the posterior cerebral arteries. Therefore, the various dimensions of the device disclosed below are chosen to suit the dimensions of the basilar artery. It is to be understood, however, that the teachings herein can be applied in the diversion of the flow in any vessel of a patient and not just the basilar artery and that it is also not restricted solely to application with aneurysms at bifurcations or elsewhere. It will be appreciated that the dimensions of the device will differ for different vessel sizes.

Figure 1:
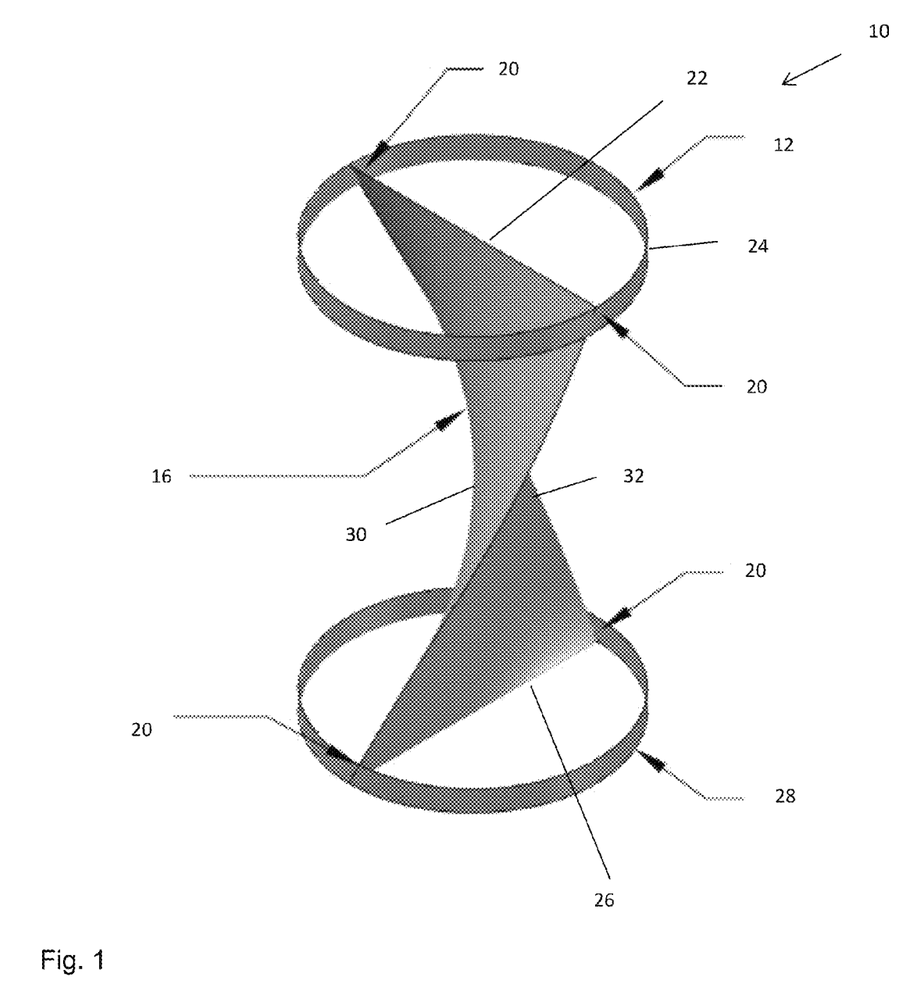
FIG. 1 is a perspective view of an embodiment of flow diverter.

Referring first to FIG. 1, there is shown a preferred embodiment of endoluminal flow diverter 10 which in this particular example is sized to fit within the basilar artery of a patient, as described in further detail below.

The flow diverter 10 includes a distal support 12 which in this embodiment is in the form of a resilient ring of generally circular form. The distal support 12 is located at the distal extremity of the flow diverter 10. A proximal support 14, again being in this embodiment in the form of an annular ring of resilient material, is located at the proximal end of the flow diverter 10. It is preferred that the distal and proximal supports 12, 14, form the distal and proximal extremities, respectively, of the flow diverter 10.

Supported by and extending between the proximal and distal supports 12, 14 is a diverter element 16 which in this example is a substantially rectangular panel made of impermeable or substantially impermeable material and which twists in the longitudinal direction of the flow diverter 10. More specifically, the panel 16 is attached at diametrically opposite sides 20 of each support 12, 14. The attachment may be by a solder joint, welding, use of bonding agent or any other suitable attachment method. In this embodiment, the panel 16 is attached to the supports 12, 14, such that the proximal edge 22 of the panel 16 is aligned with the proximal edge 24 of the distal support 12, while the distal edge 26 of the panel 16 is aligned with the distal edge 28 of the proximal support 14. In other embodiments, the edges 22, 26 of the panel 16 may be attached at any location within the length, or depth, of the support rings 12, 14.

The proximal and distal supports may be made of an elastically deformable material or a spring material such as spring steel. The supports are preferably made of a shape memory material, preferably a shape memory alloy such as nickel titanium alloy (Nitinol) or cobalt chromium. The panel 16 may be made of the same material as the proximal and distal supports 12, 14 but may be made of other materials. These materials and other materials preferably used for the device 10 are anti-thrombotic material.

In the preferred embodiments the device is made of radiopaque materials of or includes radiopaque markers. In the preferred embodiment, radiopaque markers or material are provided in the support rings 12, 14.

It will be appreciated that when made of a spring or shape memory material, the device 10 will exhibit resilience, for example compressibility in the radial direction, yet will exert a force tending it to its rest shape, that is its shape when not subjected to an external force. The device can thus be radially compressed in an introducer assembly for delivery and will expand when released for the introducer assembly constraints, in practice until it abuts and presses against the vessel walls as described in detail below. When made of a shape memory material, the device can be manufactured to have a transition temperature around body temperature and thus to exhibit its elastic return force only once delivered into the patient's vessel. For delivery purposes, the device can be twisted along its longitudinal axis, which will cause twisting and radial compression of the device, specifically by twisting of the diverter element 16 and the supports 12, 14 on themselves. Once the device is freed to revert to its non-twisted shape, that is the device is released from the introducer assembly and hence from constraining elements holding it twisted, the supports 12, 14 and the diverter element 16 will untwist to adopt the configuration shown in FIG. 1.

Figure 5:
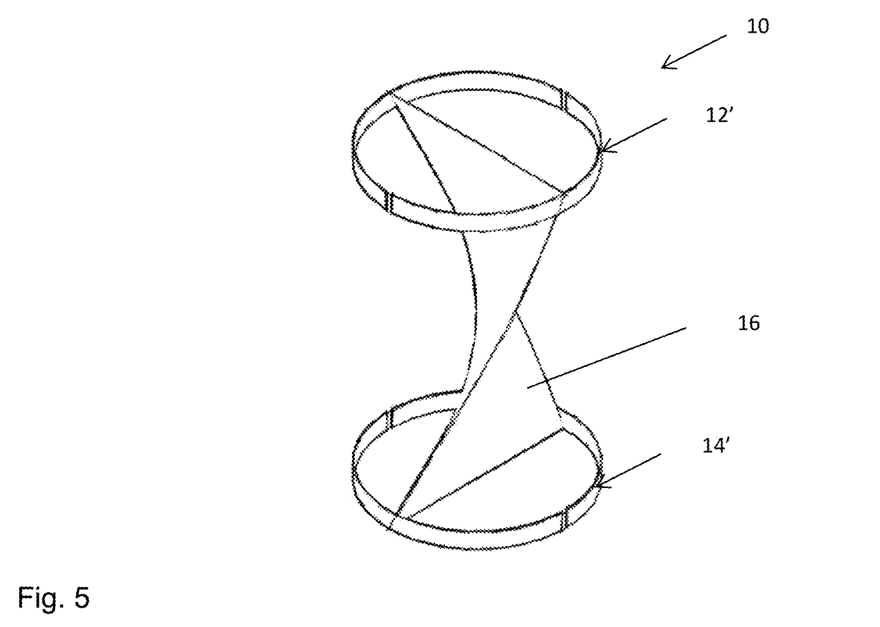
FIG. 5 is a perspective view of another embodiment of flow diverter.

The proximal and distal support rings 12, 14 may be continuous rings of strip material or wire. In other embodiments it may have other configurations, such as a split ring, or a conventional stent ring having, for example, a sinusoidal or zigzag shape for radial compressibility. Furthermore, each of the proximal and distal support rings 12, 14 may be made of a single element but could in other embodiments be a set of annular elements, such as turns of a coil, of a strip or the like. FIG. 5 shows an embodiment of device 10 in which the proximal 12' and distal 14' support elements are in the form of split rings. This structure will enhance the radial compressibility of the support elements and will still enable them to expand radially outwardly on release from the introducer assembly, thereby to provide support against the vessel wall and support to the panel 16.

Figure 2:
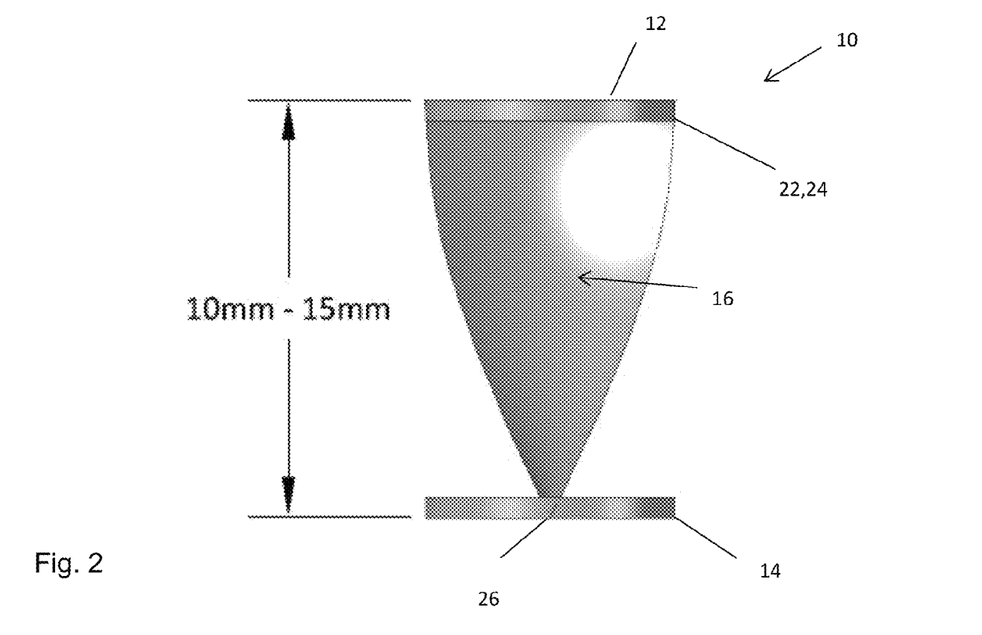
FIGS. 2 and 3 are side elevational views of the flow diverter.

Referring now to FIG. 2, there is shown a side elevational view of the flow diverter 10 of FIG. 1, from a view point perpendicular to the proximal edge 22 of the panel 16. It can be seen that the edge 22 of the flow diverter is disposed in the plane of the sheet of the drawing, whereas the distal edge 26 of the panel is at substantially 90°, being substantially perpendicular to the plane of the sheet of the drawing. In other words, the diverter element 16 is in this embodiment twisted by an angle of about 90° between its proximal and distal extremities. FIG. 2 also shows an example of the preferred lengths of the flow diverter 10 for deployment in the basilar artery. This preferred length is in the range of about 10 mm to about 15 mm.

Figure 3:
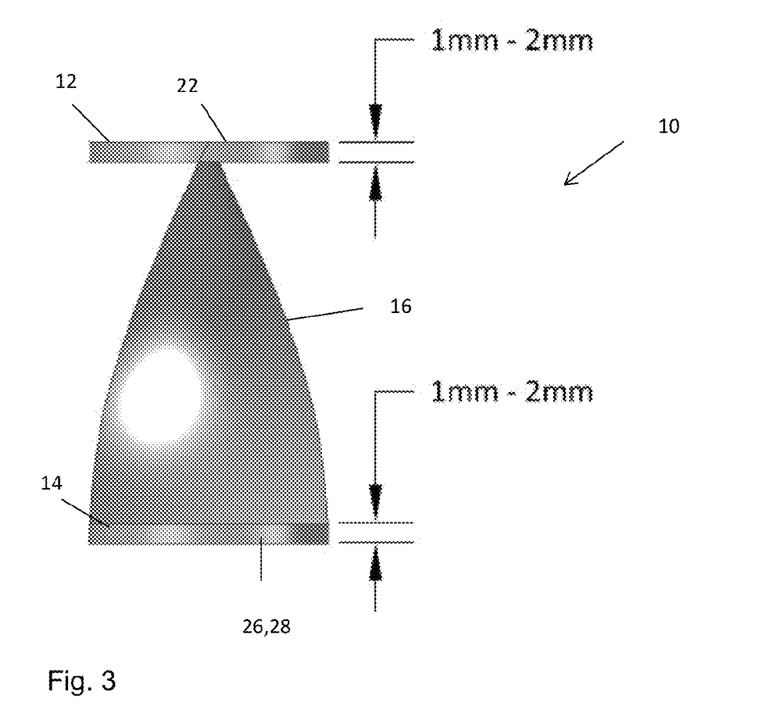

FIG. 3 is a view similar to FIG. 2 but in which the flow diverter 10 has been rotated by 90°, in which case the proximal edge 22 of the diverter element 16 is normal for the plane of the paper of the drawing, whereas the distal edge 26 of the diverter element 16 is parallel to the plane of the paper of the drawing. FIG. 3 also shows an example of the dimensions of the proximal and distal support elements 12, 14 for a flow diverter 10 for deployment in the basilar artery. In this embodiment, the proximal and distal support elements 12, 14 preferably have a depth or length in the range of about 1 mm to about 2 mm.

Figure 4:
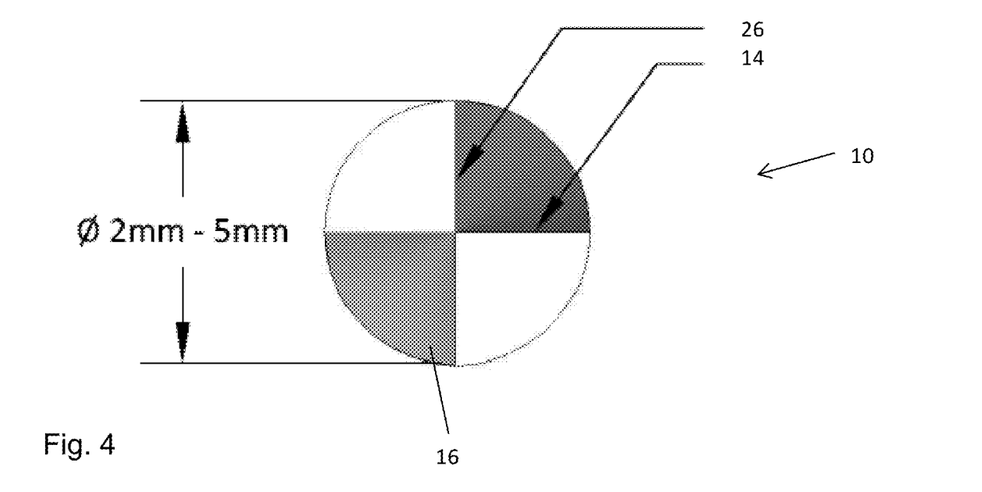
FIG. 4 is a plane view of the flow diverter.

FIG. 4 is a bottom plane view of the flow diverter 10, in which the twist of the panel 16 can be seen through the 90° of the preferred embodiment. FIG. 4 also shows the preferred diameter of the flow diverter 10, again for a diverter sized to fit within the basilar artery. In this embodiment, the diverter 10 has a diameter in the range of about 2 mm to 5 mm.

The wall thickness of the support elements 12, 14 and of the diverter element 16 is between about 0.5 mm to about 2.0 mm for a flow diverter having the dimensions given in the described example. It is to be understood that the diverter element 16 could have a greater or lesser twist than 90°, although a twist of 90° is preferred.

With reference to FIGS. 1 to 4, it will be appreciated that the flow diverter 10 is sized such that the proximal and distal supports 12, 14 fit within a patient's vessel so as to press against the internal vessel walls to keep the flow diverter in position. The side edges 30, 32 of the diverter element or panel 16 are preferably shaped and sized so as to extend to the lateral periphery of the flow diverter 10 and in particular to or close to the deployed diameter of the proximal and distal support elements 12, 14. In this regard, the thickness of the preferred support elements 12, 14 will generally be immaterial with respect to the contact of the side edges 30, 32 of the diverter element 16 with the vessel walls.

With such dimensions, the diverter element 16 will extend across the entire diameter of the vessel and will twist along the length of the flow diverter 10, such that any blood passing into the flow diverter 10 (through the patient's vessel) will be subjected to the twisting flow diverter path produced by the diverter element or panel 16. This is the preferred arrangement, namely that the entirety of fluid flow through the device 10 and through the vessel in which the device 10 is implanted is subjected to the twisting action produced by the twisted divert element or panel 16. It is not excluded, however, in some embodiments that there may be a narrow gap between the side edges 30, 32 of the diverter element 16 and the vessel walls, possible primarily because of fluid stagnation or lamination at the vessel surfaces. This latter option is, however, not generally preferred.

The provision of a diverter element 16 in the form of uniform thickness along its length and which is fixed at diametrically opposite locations on the support elements 12, 14 ensures that there is the same volume of fluid passing that the inlet of the device than leaves the outlet of the device and also either side of the panel. This ensures that there is no overall change in pressure of fluid passing through the element 10, solely a smoothing of that pressure across the cross-sectional area of the device 10 and thus of the vessel.

Figure 6:
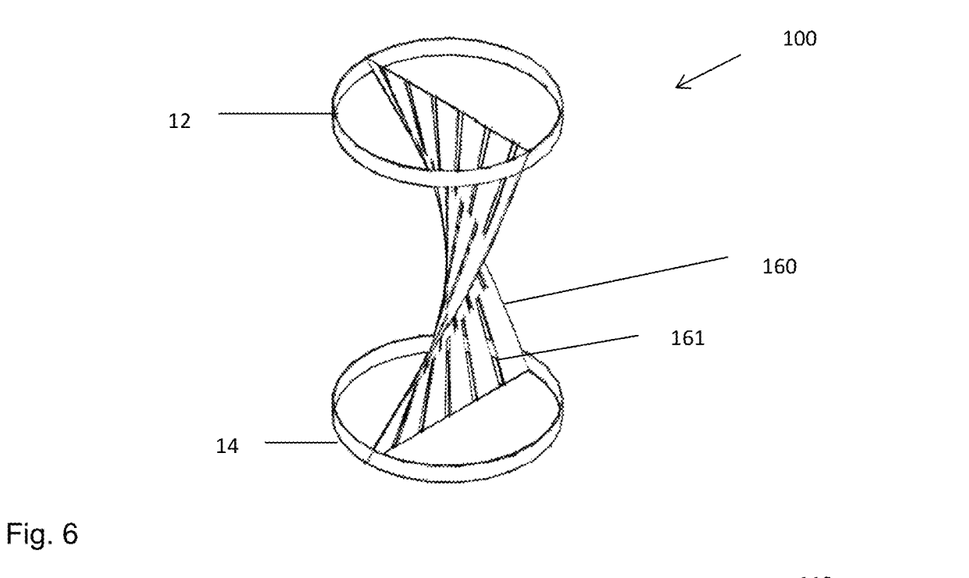
FIG. 6 is a perspective view of another embodiment of flow diverter.

Referring now to FIG. 6, there is shown another embodiment of flow diverter 100 similar to the embodiment of FIGS. 1 to 5 but in which the diverter panel 160 is formed with longitudinal slits 161 therein. The slits 161, which in some embodiments may provide no gap in the surface of the panel 160, make it easier for the panel 160 to twist on itself so as to compress the device 100 for delivery purposes. The panel 160 still provides a surface for guiding the flow of fluid through the device 100, effectively the same as a whole panel 16 as in the previous embodiments. As will be apparent in FIG. 6, the slits are in a plurality of series along the length of the panel 160, with the slits in adjacent series being laterally offset from one another. The skilled person will appreciate that the device 100 can have any of other characteristics and elements of the devices taught herein.

Figure 7:
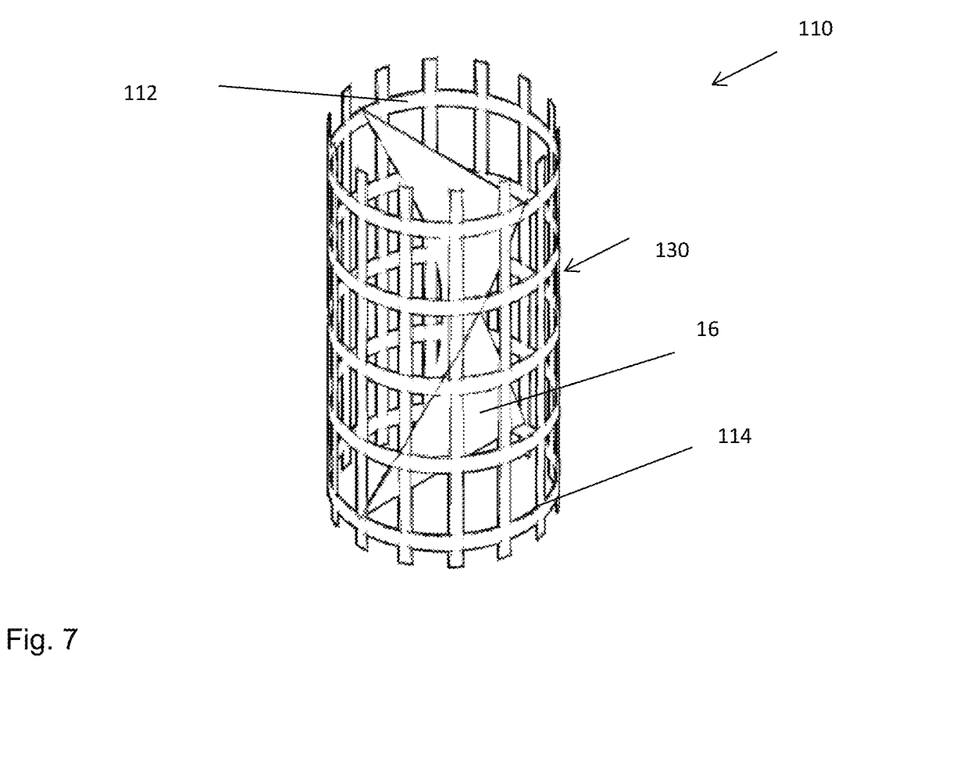
FIG. 7 is a perspective view of another embodiment of flow diverter.
Figure 8:
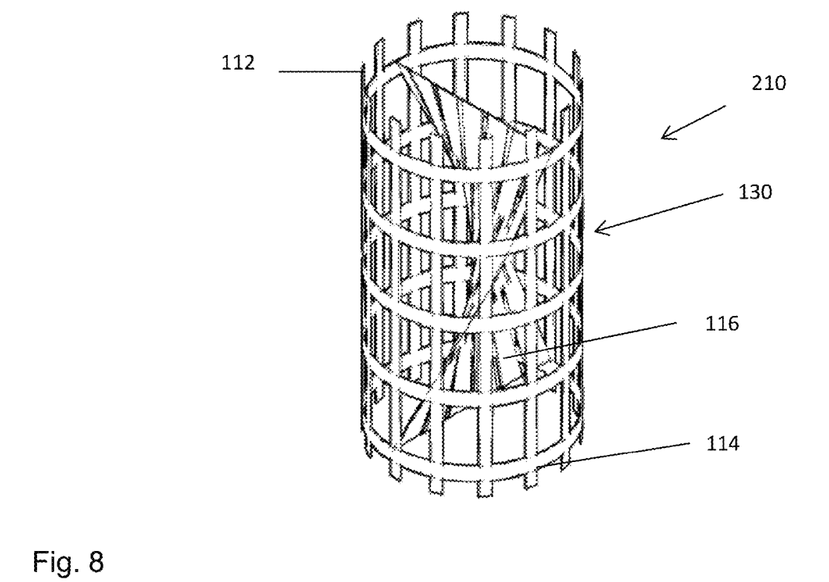
FIG. 8 is a perspective view of another embodiment of flow diverter.

FIG. 7 shows another embodiment of device 110, in which the proximal and distal support elements 112, 114 are stent rings of a stent 130 which extends for the whole length of the device 110. The stent 130 provides longitudinal support to the device 110 and to the panel 16. A similar embodiment of device 210 is shown in FIG. 8, in which the panel 116 is similar to the panel of the embodiment of FIG. 6. It will be apparent that in the embodiments of FIGS. 7 and 8, as with all the other embodiments taught herein, the supports 112, 114 may be in the form of zigzag stents, as well as taking any of the other forms taught herein.

Figure 9:
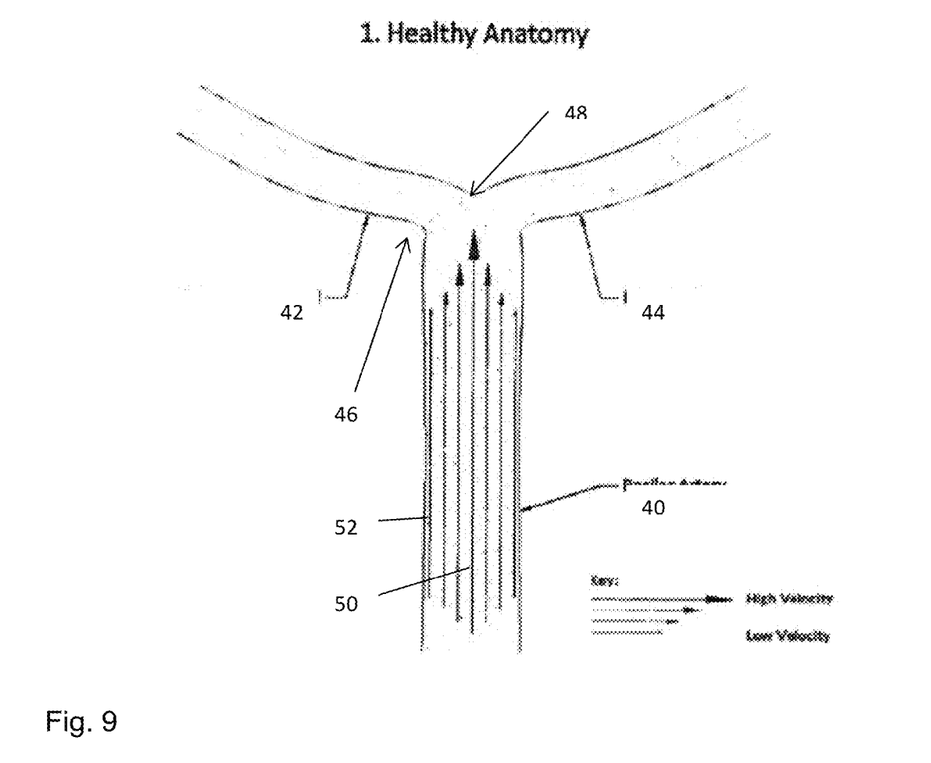
FIG. 9 is a schematic diagram of typical fluid flow in the basilar artery.

Referring now to FIG. 9, there is shown by way of illustration only a schematic diagram of a cross-section of a part of a patient's cerebral vasculature and in particular of the basilar artery 40 and its bifurcation into the right posterior cerebral artery 42 and the left posterior cerebral artery 44. In a healthy anatomy, the vessel wall opposite the bifurcation 46 exhibits an indentation 48 which assists in the guiding of blood into the posterior cerebral arteries 42, 44. The arrows 50 in FIG. 5 depict the flow of blood from the basilar artery into the right and left posterior cerebral arteries 42, 44. The size and relative positions of the arrows 50 depict the speed and strength of the flow at the various positions within the basilar artery 40. Specifically, adjacent the walls 52 of the basilar artery 40, flow is reduced, whereas towards the center of the basilar artery 40 flow is as its highest. In other words, the strength of the flow and therefore flow pressure increases from the edges of the wall 52 of the basilar artery 40 towards the center point of the artery. This is typical of laminar flow.

Figure 10:
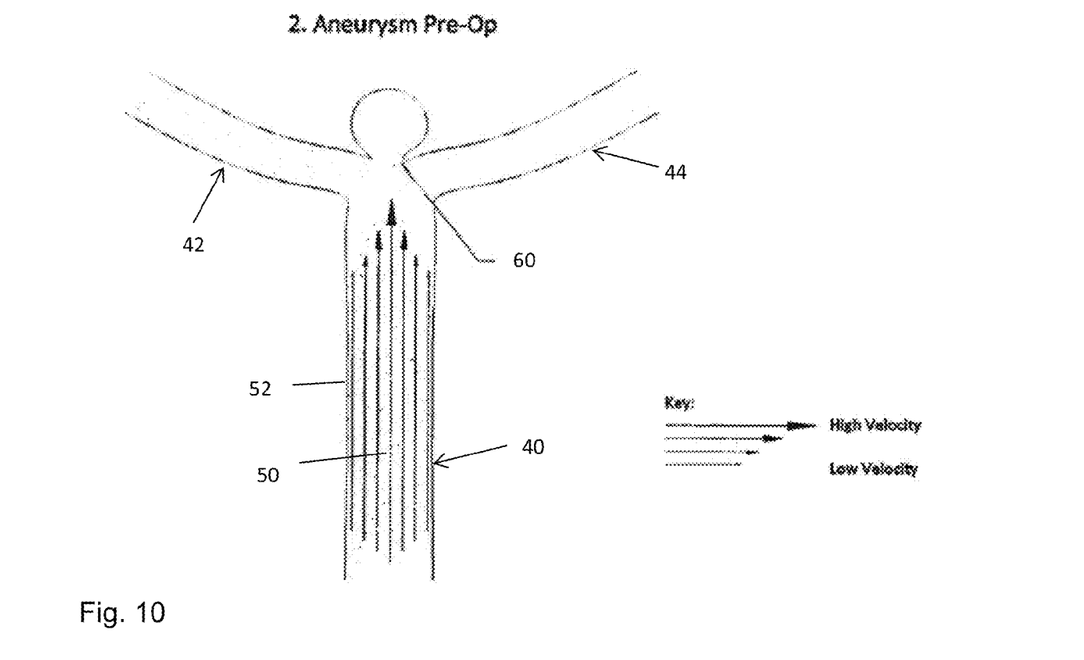
FIG. 10 is a view in which an aneurysm has formed at the bifurcation with the left and right posterior cerebral arteries.

Referring now to FIG. 10, this shows the same vessels as FIG. 9, that is the basilar artery 40 and right and left posterior cerebral arteries 42, 44, but in a patient with a developed aneurysm 60 at the point of bifurcation. This is typically caused by a weakening of the vessel wall at the point of bifurcation, the weakening creating an aneurysm sack as the result of continued pressure of blood from the basilar artery 40 to the bifurcation. The skilled person will appreciate that in a condition such as that depicted in FIG. 10, the aneurysm 60 will be subjected to the highest pressure/flow part of the blood from the basilar artery 40. This pressure will tend to cause the aneurysm sack 60 to grow in size, with consequential weakening of the vessel wall. Left untreated, this can result in the rupture of the vessel wall and of haemorrhaging.

Figure 11:
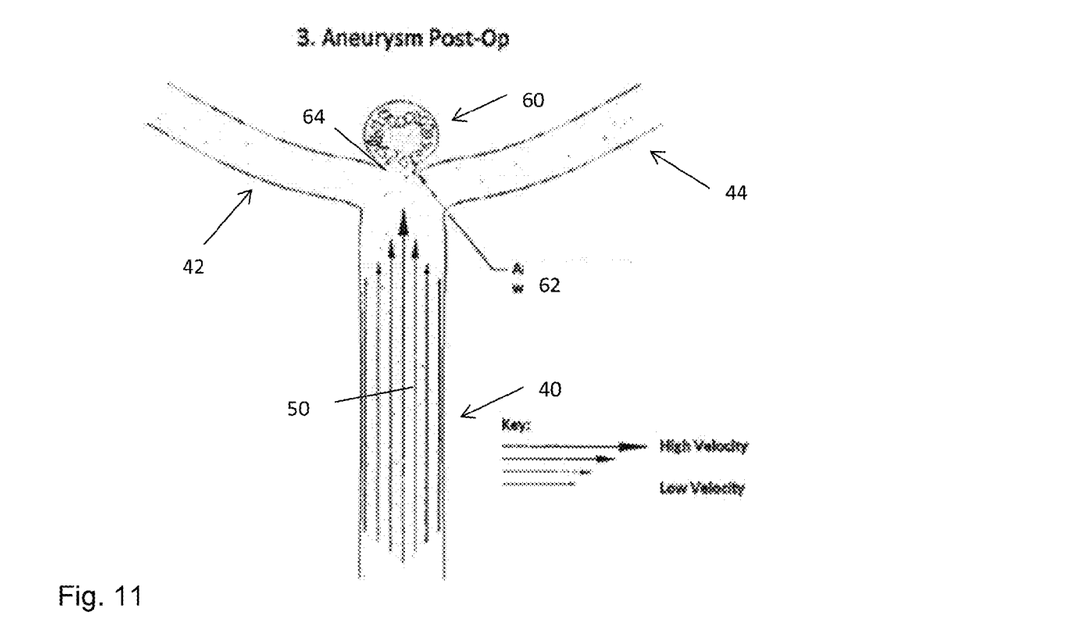
FIG. 11 is a view in which the aneurysm sac has been filled with an embolization coil.

FIG. 11 shows the vessel anatomy of FIG. 10, in which an embolization coil has been fitted into the aneurysm sack 60 in order to fill this. The purpose of the embolization coil 62 is to close off the volume of the sack 60 to prevent further flow of blood into the aneurysm sack and thereby to reduce the pressure on the walls of the vessel within the sack 60. However, as depicted in FIG. 11 there is continued flow of blood 50 towards the aneurysm sack 60, with the part of greatest flow and pressure heading directly towards the neck or opening 64 of the aneurysm 60. Thus, the flow of blood 50 will continue to apply pressure into the aneurysm.

Figure 12:
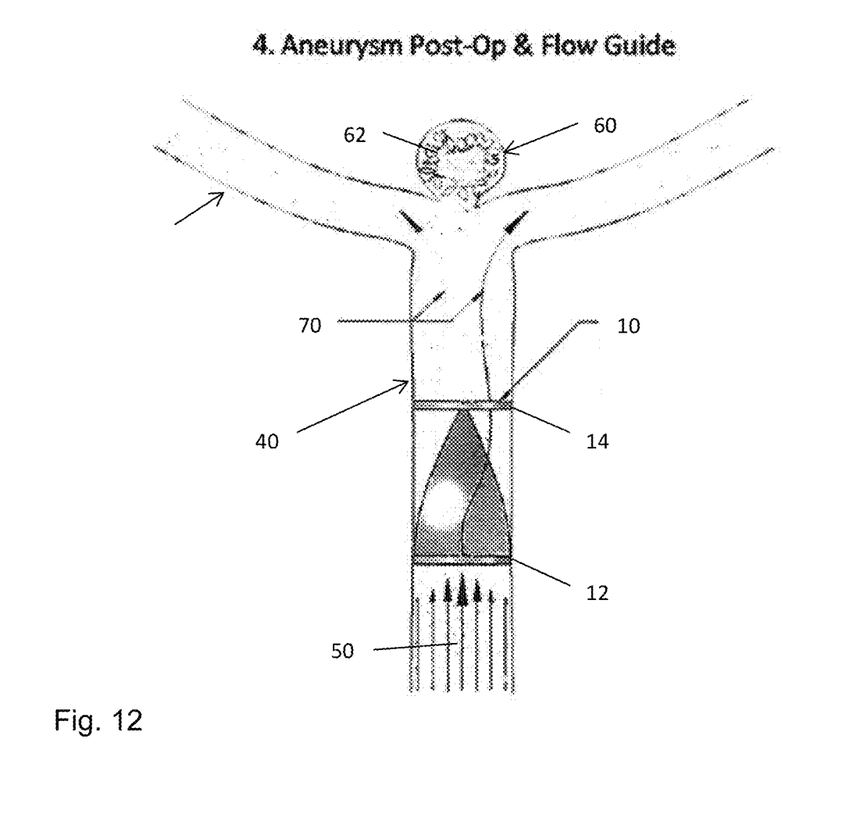
FIG. 12 is a view in which a flow diverter has been deployed in the basilar artery.

Referring now to FIG. 12, this is a view similar to FIG. 11, but in which the flow diverter 10 taught herein is deployed within the basilar artery 40. The flow diverter 10 has the effect of imparting a twist and slowing of the central portion of the flow 50 of blood in the artery 40, as shown in schematic form by the arrows 70. As a result, the flow diverter 10 causes a reduction in the flow and pressure of blood at the center point of the artery 40 and therefore towards the aneurysm 60, with a consequential reduction in the force imparted to the vessel walls at the aneurysm 60. In particular, the twist imparted to the flow 50 of blood will reduce lamination within the flow of blood and thus even out of the pressure across the diameter of vessel. Moreover, the twist or rotation imparted to the flow of blood can also reduce the flow of blood at the center of the vessel, in effect by the creation of a vortex void. This can substantially reduce pressure at the aneurysm 60 and assist in the healing thereof.

FIG. 12 shows an embolization coil 62 disposed within the aneurysm sac 60, although it is to be understood that this may not be necessary in order to treat the aneurysm 60. The diverter element or panel 16, 116 of the flow diverter preferably has an even twist along its length, although in other embodiments the diverter element 16 could have a varying twist, for instance an increasing twist from its distal end 12 to its proximal end 14, in the orientation shown in FIG. 12 and thus along the direction of fluid flow.

The diverter element 16, 116 need not be made of a spring material or shape memory material and in some embodiments could be made of a relatively soft material, or biomaterial which is absorbable or otherwise, supported in its twisted configuration by the proximal and distal support elements. In such an embodiment, the proximal and distal support elements could be coupled to one another, for example by appropriate struts or tethers. Struts or tethers of such a nature could be provided in all of the embodiments disclosed herein.

In other embodiments, the proximal and distal support elements could be connected together or a part of a singular support element. Such a support element could be a sleeve extending for the length of the flow diverter, in one example being in the form of a stent as shown in FIGS. 7 and 8.

It is to be appreciated that the embodiments of flow diverter taught herein may be provided with other features commonly found with implantable medical devices, for example anchoring elements in the form of barbs or the like, retrieval elements such as hooks and the like for withdrawing device from a patient's vessel after completion of a medical procedure. It is envisaged also that the device could be retained permanently within a patient's vessel, not just to treat a formed aneurysm but also in order to prevent the formation of aneurysms or further aneurysms over time.

All optional and preferred features and modifications of the described embodiments and dependent claims are usable in all aspects of the disclosure taught herein. Furthermore, the individual features of the dependent claims, as well as all optional and preferred features and modifications of the described embodiments are combinable and interchangeable with one another. It will be understood that this invention is not limited to the disclosed embodiments, as those having skill in the art may make various modifications without departing from the scope of the following claims.

The invention claimed is:

1. An endoluminal flow diverter comprising:
    a central axis running through a diameter and along a longitudinal direction;
    a proximal support and a distal support disposed along the longitudinal direction, the diverter comprising a stent, each of the proximal support and the distal support being a stent ring of the stent, the stent extending from the proximal support to the distal support;
    a diverter element being disposed between and supported by the proximal and distal supports, the diverter element comprising a panel being twisted in a helical manner in the longitudinal direction and extending across the diameter, wherein the panel twists by an angle of about 90 degrees between the proximal and distal supports.

2. An endoluminal flow diverter of claim 1, wherein the panel is substantially impermeable.

3. An endoluminal flow diverter comprising:
    a central axis running through a diameter and along a longitudinal direction;
    a proximal support and a distal support disposed along the longitudinal direction;
    a diverter element being disposed between and supported by the proximal and distal supports, the diverter element comprising a panel being twisted in the longitudinal direction and extending across the diameter, wherein the panel twists by an angle of about 90 degrees between the proximal and distal supports, and
    wherein the panel comprises a plurality of perforations therein, the panel providing a surface within which the perforations are disposed, wherein the perforations are small enough to substantially prevent flow of fluid through the panel.

4. An endoluminal flow diverter of claim 1, wherein the panel extends substantially across the diameter of the device.

5. An endoluminal flow diverter of claim 1, wherein the panel is of uniform thickness.

6. An endoluminal flow diverter of claim 1, wherein the panel extends across the central axis of the device.

7. An endoluminal flow diverter of claim 1, wherein the panel is rectangular.

8. An endoluminal flow diverter of claim 3, wherein the proximal and distal supports are ring-shaped.

9. An endoluminal flow diverter of claim 3, wherein the proximal and distal supports are radially compressible.

10. An endoluminal flow diverter of claim 3, wherein the proximal and distal supports are made of a spring material.

11. An endoluminal flow diverter of claim 3, wherein the proximal and distal supports are made of a shape memory material.

12. An endoluminal flow diverter of claim 3, wherein the proximal and distal supports are separate from one another.

13. An endoluminal flow diverter of claim 1, wherein the panel extends across the entire diameter of the device.

14. An endoluminal flow diverter of claim 1, wherein the panel has a uniform twist between the proximal and distal supports.

15. The endoluminal flow diverter of claim 3, wherein the panel extends substantially across the diameter of the device.

16. The endoluminal flow diverter of claim 3, wherein the panel is of uniform thickness.

17. The endoluminal flow diverter of claim 3, wherein the panel extends across the central axis of the device.

18. The endoluminal flow diverter of claim 3, wherein the panel is rectangular.

19. The endoluminal flow diverter of claim 3, wherein the panel extends across the entire diameter of the device.

20. The endoluminal flow diverter of claim 3, wherein the panel has a uniform twist between the proximal and distal supports.

\* \* \* \* \*